US 6,751,504 B2

(12) United States Patent
Fishler

(10) Patent No.: US 6,751,504 B2
(45) Date of Patent: Jun. 15, 2004

(54) SYSTEM AND METHOD FOR BI-CHAMBER STIMULATION USING DYNAMICALLY ADAPTED INTERPULSE DELAY

(75) Inventor: Matthew G. Fishler, Huntington, NY (US)

(73) Assignee: Pacesetter, Inc., Sylmar, CA (US)

( * ) Notice: Subject to any disclaimer, the term of this patent is extended or adjusted under 35 U.S.C. 154(b) by 85 days.

(21) Appl. No.: 09/866,141

(22) Filed: May 25, 2001

(65) Prior Publication Data

US 2002/0177880 A1 Nov. 28, 2002

(51) Int. Cl.[7] .................................................. A61N 1/365
(52) U.S. Cl. ........................................... 607/25; 607/27
(58) Field of Search ................................ 607/9, 25, 27, 607/28

(56) References Cited

U.S. PATENT DOCUMENTS

| 5,267,560 A | * 12/1993 | Cohen | 607/25 |
| 5,466,254 A | 11/1995 | Helland | 607/123 |
| 5,540,727 A | 7/1996 | Tockman et al. | 607/18 |
| 5,584,868 A | 12/1996 | Salo et al. | 607/17 |
| 5,626,620 A | * 5/1997 | Kieval et al. | 607/28 |
| 5,700,283 A | 12/1997 | Salo | 607/17 |
| 5,720,768 A | 2/1998 | Verboven-Nelissen | 607/9 |
| 5,800,471 A | 9/1998 | Baumann | 607/25 |
| 5,902,324 A | 5/1999 | Thompson et al. | 607/9 |
| 6,044,298 A | 3/2000 | Salo et al. | 607/17 |
| 6,122,545 A | 9/2000 | Struble et al. | 607/9 |
| 6,411,848 B2 | * 6/2002 | Kramer et al. | 607/9 |
| 2002/0133198 A1 | * 9/2002 | Kramer et al. | 607/9 |

OTHER PUBLICATIONS

Cazeau, S. et al., Four Chamber Pacing in Dilated Cardiomyopathy, PACE, vol. 17, Part 2, pp. 1974–1979 (Nov. 1994).

* cited by examiner

Primary Examiner—George R. Evanisko

(57) ABSTRACT

An implantable stimulation device and associated method allow for the selection of an inter-ventricular or inter-atrial delay which results in optimal hemodynamic benefit for the patient. The stimulation device monitors and measures the width of the QRS complex, or a P wave in response to different interpulse delays during biventricular or biatrial stimulation. The stimulation device then selects the optimal interpulse delay that results in the minimum QRS or P width. The present method allows for the adaptive adjustment of the interpulse interval over time, caused for example, by changes in disease state, medical therapy, physical activity or other factors may cause changes in the electromechanical response of the heart.

29 Claims, 4 Drawing Sheets

SYSTEM AND METHOD FOR BI-CHAMBER STIMULATION USING DYNAMICALLY ADAPTED INTERPULSE DELAY

FIELD OF THE INVENTION

This invention relates generally to programmable cardiac stimulating devices. More specifically, the present invention is directed to an implantable stimulation device and associated method that allow for the selection of an inter-atrial or inter-ventricular stimulation delay which results in optimal hemodynamic benefit for the patient.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave, also referred to as the QRS complex, and the resulting ventricular chamber contractions. Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or other anti-arrhythmia therapies to the heart at a desired energy and rate. One or more heart chambers may be electrically stimulated depending on the location and severity of the conduction disorder.

Cardiac pacemakers conventionally stimulate a heart chamber by applying current pulses to cardiac tissues via two electrodes, a cathode and an anode. Standard pacing leads are available in either of two configurations, unipolar leads or bipolar leads. A unipolar lead has a single cathodic electrode with the anode being the pacemaker housing. A bipolar lead possesses two electrodes located 1 to 2 cm apart.

A single-chamber pacemaker delivers pacing pulses to one chamber of the heart, either one atrium or one ventricle, via either a unipolar or bipolar lead. Single-chamber pacemakers can operate in either a triggered mode or a demand mode. In a triggered mode, a stimulation pulse is delivered to the desired heart chamber at the end of a defined time-out interval to cause depolarization of the heart tissue (myocardium) and its contraction. The stimulating pulse must be of sufficient energy to cause depolarization of the heart chamber, a condition known as "capture." The lowest pulse energy required to achieve capture is termed "threshold." The pacemaker also delivers a stimulation pulse in response to a sensed event arising from that chamber when operating in a triggered mode.

When operating in a demand mode, sensing and detection circuitry allow for the pacemaker to detect if an intrinsic cardiac depolarization, either an R-wave or a P-wave, has occurred within the defined time-out interval. If an intrinsic depolarization is not detected, a pacing pulse is delivered at the end of the time-out interval. However, if an intrinsic depolarization is detected, the pacing pulse output is inhibited to allow the natural heart rhythm to preside. The difference between a triggered and demand mode of operation is the response of the pacemaker to a detected native event.

Dual chamber pacemakers are now commonly available and can provide either trigger or demand type pacing in both an atrial chamber and a ventricular chamber, typically the right atrium and the right ventricle. Both unipolar or bipolar dual chamber pacemakers exist in which a unipolar or bipolar lead extends from an atrial channel of the dual chamber device to the desired atrium (e.g. the right atrium), and a separate unipolar or bipolar lead extends from a ventricular channel to the corresponding ventricle (e.g. the right ventricle). In dual chamber, demand-type pacemakers, commonly referred to as DDD pacemakers, each atrial and ventricular channel includes a sense amplifier to detect cardiac activity in the respective chamber and an output circuit for delivering stimulation pulses to the respective chamber. If an intrinsic atrial depolarization signal (a P-wave) is not detected by the atrial channel, a stimulating pulse will be delivered to depolarize the atrium and cause contraction. Following either a detected P-wave or an atrial pacing pulse, the ventricular channel attempts to detect a depolarization signal in the ventricle. If no R-wave is detected within a defined atrial-ventricular interval (AV interval or AV delay), a stimulation pulse is delivered to the ventricle to cause ventricular contraction. In this way, rhythmic dual chamber pacing is achieved by coordinating the delivery of ventricular output in response to a sensed or paced atrial event.

Over the years, dual-chamber stimulation has been found to provide clinical benefit to patients suffering from congestive heart failure and other cardiac abnormalities. It has also been found that the optimization of timing intervals during stimulation may be critical in providing hemodynamic benefit. Numerous schemes for optimizing the AV delay in order to improve cardiac function have been proposed. Reference is made, for example, to U.S. Pat. No. 5,540,727 to Tockman et al; U.S. Pat. No. 5,584,868 to Salo et al.; and U.S. Pat. No. 6,044,298 to Salo et al. Such schemes often incorporate sensors designed to assess cardiac function by monitoring blood pressure, pulse pressure, cardiac impedance, cardiac wall motion, heart sounds and other similar parameters.

In patients suffering from congestive heart failure, dilation of the heart can alter normal conduction pathways. Conduction through the heart chambers can become slower or inter-atrial or inter-ventricular conduction delays can develop. Thus, synchronizing the right and left heart chambers during bi-ventricular, bi-atrial, or multi-chamber stimulation may be vital to improving cardiac output. Mounting clinical evidence supports the evolution of more complex cardiac stimulating devices capable of stimulating three or even all four heart chambers to stabilize arrhythmias or to re-synchronize heart chamber contractions (see Cazeau S. et al., "Four chamber pacing in dilated cardiomyopathy," *Pacing Clin. Electrophsyiol* 1994 17(11 Pt 2):1974–9).

One limitation of some multi-chamber stimulation systems is that stimulation of left and right heart chambers is simultaneous. Simultaneous contraction of both left and right chambers is not physiological and is not always necessary or desirable in a given patient. Proposed systems provide a delay between the stimulation of opposing heart chambers. Reference is made to U.S. Pat. No. 5,720,768 to Verboven-Nelissen; U.S. Pat. No. 5,902,324 to Thompson et al.; and U.S. Pat. No. 6,122,545 to Struble et al. While programmable inter-ventricular or inter-atrial delay intervals have been proposed, the selection of such intervals may be arbitrary.

Ideally, a direct measure of cardiac hemodynamics would be the best way to monitor the benefit of stimulation and provide feedback for making adjustments to stimulation timing intervals. However, direct measures such as left ventricular ejection fraction are impossible to perform chronically at the present time. Methods proposed previously for optimizing AV delay during dual chamber stimulation directed at maximizing hemodynamic performance are limited by the need for additional sensors and more complex software algorithms and may not apply to the optimization of inter-atrial timing or inter-ventricular timing.

Therefore, there remains an unmet need for a multi-chamber cardiac stimulation device that allows for the selection of an inter-atrial or inter-ventricular delay that results in optimal hemodynamic benefit for the patient. It would thus be desirable to provide automatic optimization of the delay between left and right heart chamber stimulation that could be adaptive over time, thereby adjusting the stimulation delay as needed with changes in disease state. It would also be desirable to provide such automatic, adaptive adjustment of this stimulation delay without requiring additional sensors or complex hardware.

SUMMARY OF THE INVENTION

The present invention addresses these needs by providing a method for optimizing the ventricular (or atrial) interpulse delay, that is the time between left and right ventricular (or atrial) chamber pulse delivery, during biventricular (or biatrial) stimulation. The present invention advantageously measures the width of the QRS complex. Since a narrow QRS complex, that is a relatively short ventricular depolarization signal, generally implies a more uniform contraction of the right and left ventricles, a more uniform contraction is associated with a more effective hemodynamic performance of the cardiac stimulation device.

Conduction abnormalities that cause inter- or intra-ventricular conduction delays produce less synchronized contractions of the right and left ventricles that can be recognized by a widened QRS complex. Thus, by monitoring the QRS width in response to different interpulse delays during biventricular stimulation, the optimal interpulse delay setting that results in the minimum QRS width and presumably the most optimal hemodynamic benefit can be determined.

Thus, one feature of the present invention is a method for sensing and measuring the QRS width. Sensing the QRS complex may be done using the same electrodes used for stimulating the ventricles (near-field sensing), but preferably is done using electrodes that are not in direct contact with the ventricles (far-field sensing) in order to make a global measurement of the ventricular depolarization.

Another feature of the present invention is an algorithm that allows comparisons of the QRS width measured during biventricular stimulation at different interpulse delays. Preferably a convergent, iterative algorithm is used to identify the interpulse delay producing the minimum QRS width.

Yet another feature of the present invention is the adaptive adjustment of the interpulse interval over time. Since changes in disease state, medical therapy, physical activity or other factors may cause changes in the electromechanical response of the heart, the optimal interpulse interval may change over time. Therefore, the present invention includes periodic, automatic execution of the interpulse delay optimization algorithm so that the interpulse delay is automatically adjusted over time, as needed.

In still another embodiment of the invention, the width of P waves are measured during biatrial pulsing. An optimal interpulse delay is selected by determining the P wave having the minimum width, and selecting the associated interpulse delay that caused such P wave.

BRIEF DESCRIPTION OF THE DRAWINGS

The various features of the present invention and the manner of attaining them will be described in greater detail with reference to the following description, claims, and drawings, wherein reference numerals are reused, where appropriate, to indicate a correspondence between the referenced items, and wherein:

DESCRIPTION OF THE PREFERRED EMBODIMENTS

The following description is of a best mode presently contemplated for practicing certain preferred embodiments of the present invention. This description is not to be taken in a limiting sense but is made merely for the purpose of describing the general principles of the invention.

As indicated above, the present invention relates to a method for optimizing the interpulse delay between stimulation of the right and left ventricles in order to maximize the hemodynamic benefit provided during biventricular or multi-chamber stimulation. The method of optimizing the interpulse delay is based on minimizing the width of the QRS complex as will be more fully described in conjunction with FIG. 4. The method described herein is intended for use in any cardiac stimulation device that is capable of delivering both right and left ventricular stimulations. One such device will now be described in conjunction with FIGS. 1 and 2.

Figure 1:
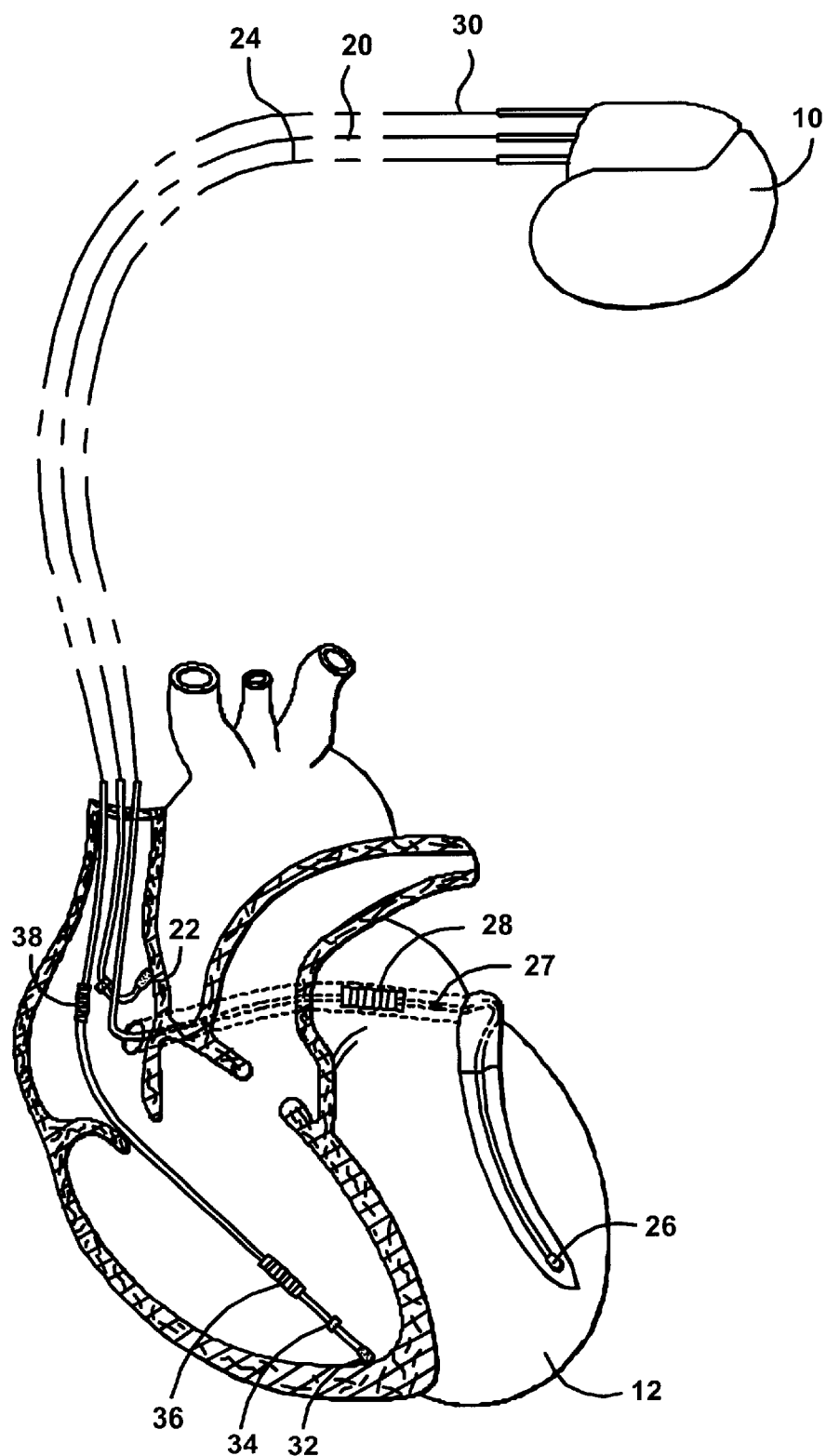
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, entitled "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC (superior vena cava) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
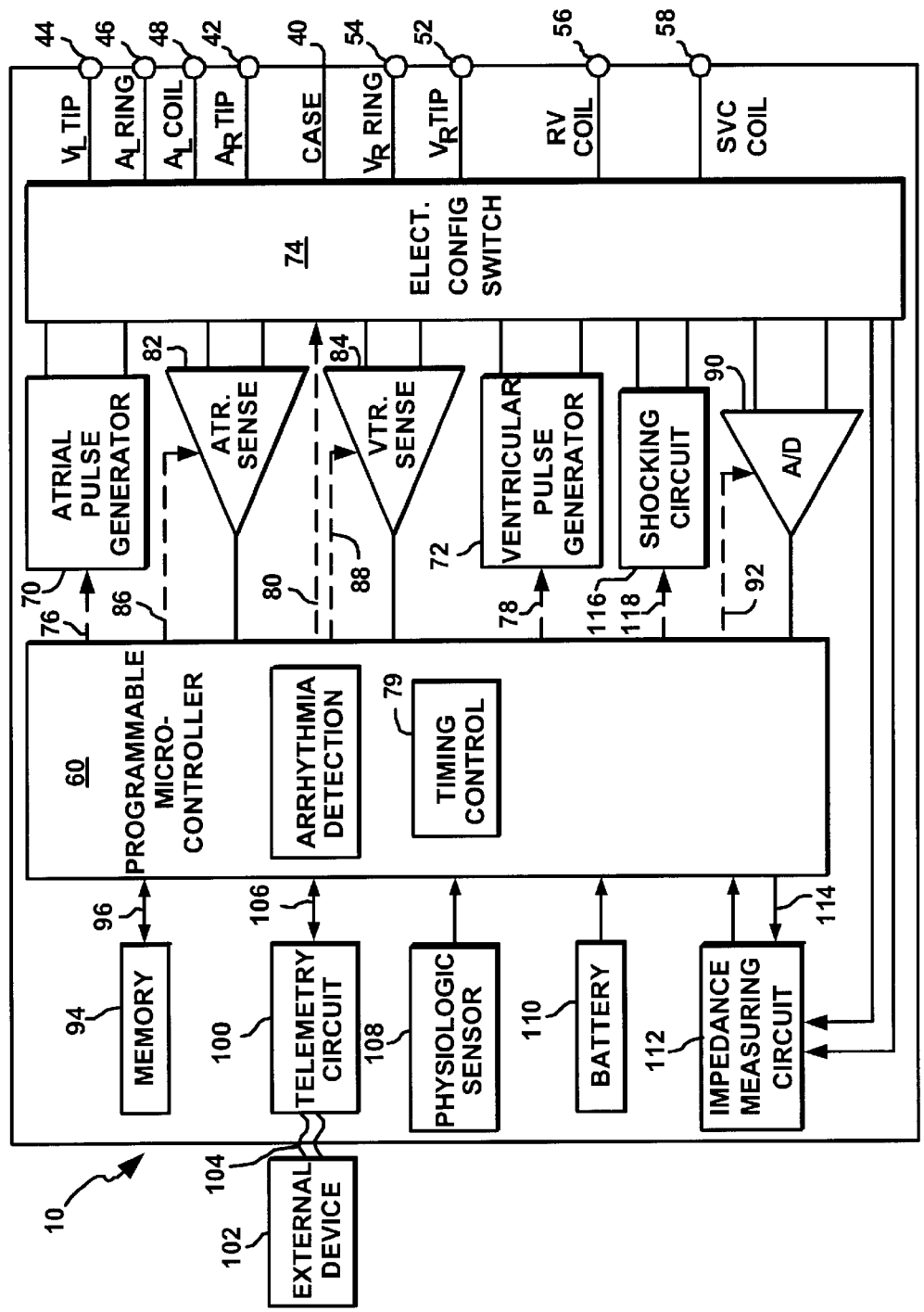
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. As used herein, the shape of the stimulation pulses is not limited to an exact square or rectangular shape, but may assume any one of a plurality of shapes which is adequate for the delivery of an energy packet or stimulus.

It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

In accordance with one embodiment of the present invention, far-field sensing of the QRS signal is preferred over near-field sensing. Thus, during the execution of the algorithm to be described below in which the QRS signal is measured, the desired electrode pair for sensing the QRS signal will be connected to the appropriate atrial or ventricular sensing circuit 82 or 84 through switch 74.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, antitachycardia pacing, cardioversion shocks or defibrillation shocks, collectively referred to as "tiered therapy").

The stimulation device 10 additionally includes a power source, such as a battery 110 that provides operating power to all the circuits shown in FIG. 2. For the stimulation device 10, which employs shocking therapy, the battery 110 is preferably capable of operating at low current drains for long periods of time, and also be capable of providing high-current pulses (for capacitor charging) when the patient requires a shock pulse. The battery 110 must also preferably have a predictable discharge characteristic so that elective replacement time can be detected.

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetry transmission to an external device 102. The data acquisition system 90 is coupled to the right atrial lead 20, the coronary sinus lead 24, and the right ventricular lead 30 through the switch bank 74 to sample cardiac signals across any pair of desired electrodes. In the present invention, the data acquisition system 90 will be used to collect and digitize the QRS portion of the intracardiac electrogram signal for the purpose of measuring the QRS duration or QRS width.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. In the present invention, the memory 94 will be used to store QRS width data such that measurements made of the QRS width during biventricular stimulation delivered at different interpulse intervals can be compared. Microcontroller 60 controls the delivery of biventricular stimulation by ventricular pulse generator 72 according to the programmed interpulse interval stored in memory 94. Whenever the optimization algorithm included in the present invention is performed, the interpulse delay resulting in the minimum QRS width is determined and stored in memory 94 to be used thereafter in delivering biventricular stimulation.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through an established communication link 104.

In a preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. Changes in activity as detected by physiological sensor 108 may be used by the present invention for triggering an algorithm that redetermines the optimal interpulse delay when both the right and left ventricles are stimulated.

While the physiologic sensor 108 is shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors that sense the oxygen content of blood, pressure, cardiac output, ejection fraction, stroke volume, end diastolic volume, end systolic volume, respiration rate and/or minute ventilation, pH of blood, ventricular gradient, etc. However, any sensor may be used which is capable of sensing a physiological parameter that corresponds to the exercise state of the patient.

The stimulation device 10 further includes a magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that an external programmer 102 is in place to receive or transmit data to the microcontroller 60 through the telemetry circuit 100.

As further shown in FIG. 2, the stimulation device 10 is shown as having an impedance measuring circuit 112 which is enabled by the microcontroller 60 by a control signal 114. Certain applications for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of the heart valves, etc. The impedance measuring circuit 112 is advantageously coupled to the switch 74 so that any desired electrode may be used.

In the case where the stimulation device 10 is intended to operate as an implantable cardioverter/defibrillator (ICD) device, it needs to detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
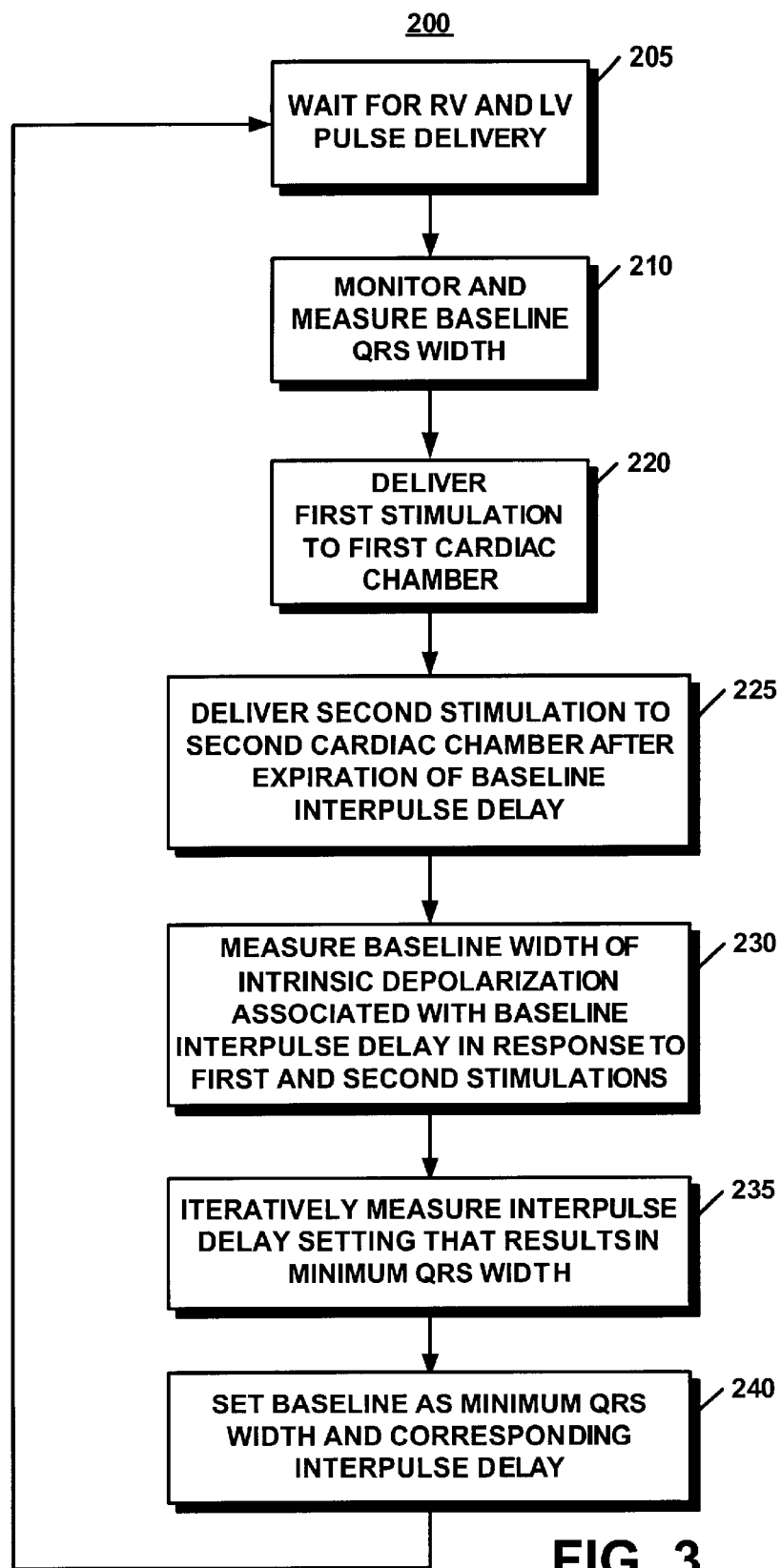
FIG. 3 is a flow chart illustrating a high level overview of the operation of one embodiment of the present invention for automatically setting the optimal ventricular interpulse delay.

In FIG. 3, a flow chart is shown describing an overview of the operation and novel features implemented in one embodiment of the stimulation device 10. In this flow chart, and the flow chart of FIG. 4, the various algorithmic steps are summarized in individual "blocks". Such blocks describe specific actions or decisions that must be made or carried out as the algorithm proceeds. Where the microcontroller 60 (or its equivalent) is employed, the flow charts presented herein provide the basis for a "control program" that may be executed or used by such a microcontroller 60 (or its equivalent) to effectuate the desired control of the stimulation device 10. Those skilled in the art may readily write such a control program based on the flow charts and other descriptions presented herein.

Figure 4:
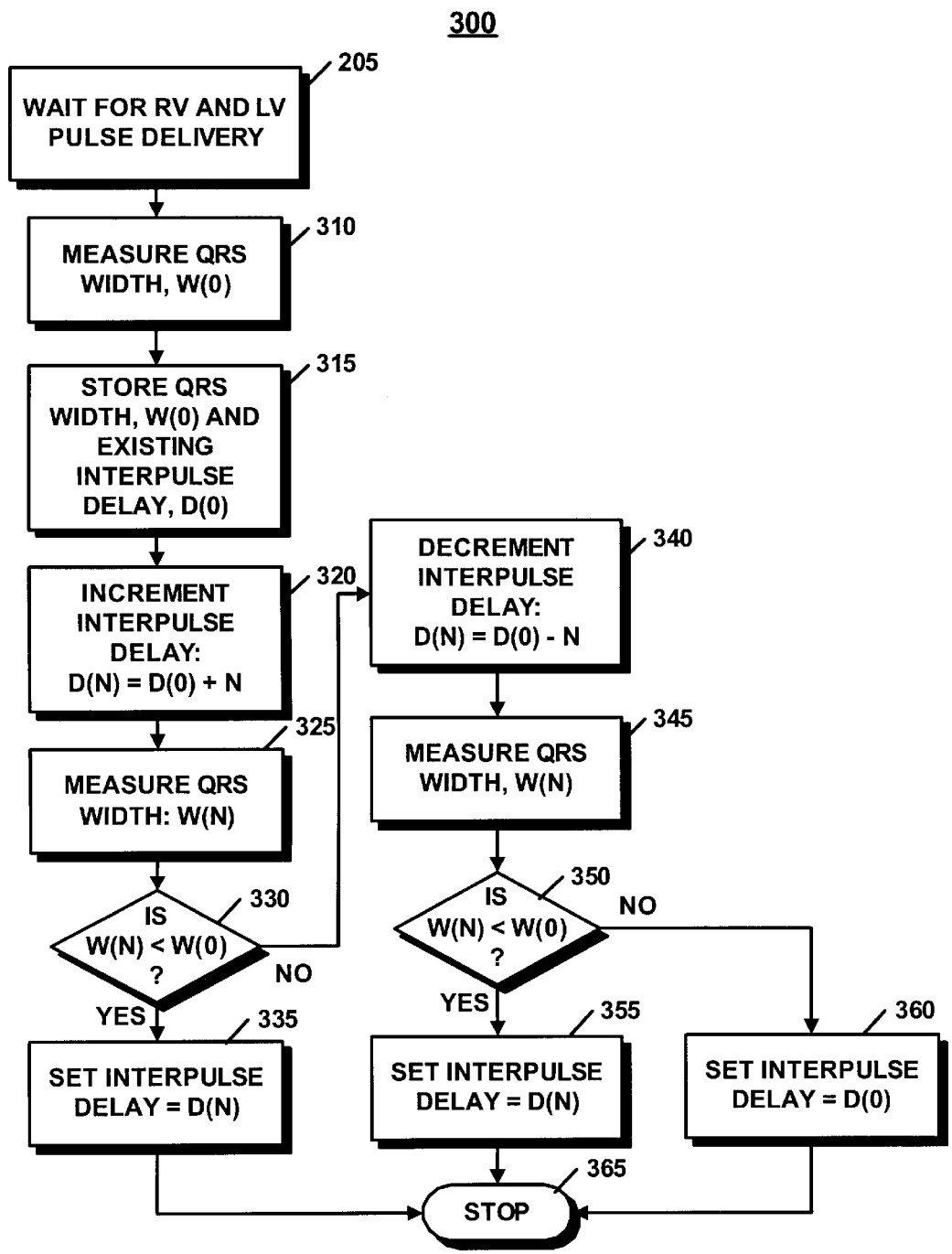
FIG. 4 is a flow chart illustrating a more detailed description of the operation for automatically setting the optimal ventricular interpulse delay of FIG. 3.

The optimization methods or algorithms 200 and 300 of FIGS. 3 and 4, respectively are performed periodically, the frequency of which is preferably programmable. Since changes in the optimal interpulse delay are expected to occur over relatively long periods of time, such as hours, days, weeks, or months, the methods 200 and 300 do not need to be performed on a beat-by-beat basis. Therefore, the methods 200 and 300 may be performed once a day, for example when the patient is at rest. The methods 200 and 300 may also be performed on a periodic basis determined by a given number of heart cycles or a change in activity level as indicated by physiological sensor 108. The frequency which method 300 is performed may thus be tailored to individual patient need as determined by a medical practitioner.

Once microprocessor 60 initiates the optimization method 200 of FIG. 3, the next ventricular stimulation pulses are delivered at step 205 at the existing, programmed interpulse delay and according to the standard timing operation of device 10. At step 210, the device 10 monitors and measures a baseline QRS width, and at step 215, the device 10 sets a baseline interpulse delay between a stimulation of a first cardiac chamber on one side of a heart and a stimulation of a second cardiac chamber on another side of the heart.

At step 220, the device 10 delivers a first stimulation to the first cardiac chamber, and, at step 225, it further delivers a second stimulation to the second cardiac chamber after the baseline interpulse delay has transpired. At step 230, the device 10 measures a baseline width of an intrinsic depolarization associated with the baseline interpulse delay, in response to the first and second stimulations. The device 10 then iteratively determines at step 235 an optimal interpulse delay that results in an optimum width of the intrinsic depolarization. At step 240, the device 10 sets the baseline as the minimum QRS width with its corresponding interpulse delay.

Once microprocessor 60 initiates the method 300 FIG. 4, the next ventricular stimulation pulses are delivered at step 205 at the existing, programmed interpulse delay and according to the standard timing operation of device 10. At step 310, the QRS width is measured. In order to measure the QRS width, the electrogram signal is sampled preferably from a far-field electrode pair, e.g. preferably an electrode pair in which neither electrode has direct contact with either ventricle. Far-field sensing of the QRS signal is preferred because a more global measurement of total ventricular function can be made rather than a more localized measurement. For example, a global QRS signal may be sensed using the SVC coil electrode 38 and the device housing 40.

In an alternative embodiment, the same electrodes used for stimulating the ventricles may also be used for sensing the QRS signal. In this embodiment, sensing may be performed between the right ventricular tip electrode 32 and the housing 40, the left ventricular tip electrode 26 and the housing 40, or between the right ventricular tip electrode 32 and the left ventricular tip electrode 34. Such sensing may not be the optimal sensing configuration because it provides a more localized measurement of ventricular depolarization. However, by providing a programmable sensing configuration, the medical practitioner may select the most suitable sensing configuration on a patient-by-patient basis.

The sensed signal is received by the appropriate sensing circuit. If a far-field signal is sensed, the signal may be received by atrial sensing circuit 82 (FIG. 2). If a more localized signal is sensed, the signal may be received by ventricular sensing circuit 84 (FIG. 2). In either case the sensed QRS complex is sampled and digitized by A/D converter 90, and this data is used to determine the QRS width according to step 310 of method 300 (FIG. 4).

The QRS width may be determined by generating a template from the digitized signal and measuring the time between two sample points indicating when the QRS signal first exceeds a given sensing threshold and when the QRS signal first goes below the same, or another, sensing threshold. Numerous methods may be used for measuring the QRS width. Any suitable technique that provides consistency in measuring the QRS width, such that reliable comparisons between measurements are possible, may be employed.

In an alternative embodiment, more than one QRS width from more than one stimulation cycle using the same interpulse delay may be measured. In this way, an average QRS width, or some other statistical measure of QRS width, for a given interpulse delay may be determined.

At step 315, the measured QRS width is stored in memory 94 as W(0). This is the QRS width associated with the existing interpulse delay setting D(0). The interpulse delay D(0) and its associated QRS width W(0) thus represent the baseline setting and measurement, respectively, for the optimization method 300.

At step 320, the baseline interpulse delay setting D(0) is incremented to a new, longer interpulse delay setting, D(N), by adding a pre-defined interval, N, to the baseline interpulse delay setting D(0), as expressed by the following equation:

$$D(N)=D(0)+N.$$

At step 325, the QRS width is measured again to obtain the new QRS width, W(N), associated with the new interpulse delay setting, D(N). This new QRS width, W(N), is compared to the baseline QRS width, W(0), at decision step 330. If the new QRS width, W(N), is less than the baseline QRS width, W(0), the new interpulse delay setting D(N) is presumed to be producing better synchronized ventricular contraction. Thus, the new interpulse delay D(N) is considered more optimal than the baseline interpulse delay D(0), and the interpulse delay setting is kept at the new setting D(N) at step 335, and the method 300 is terminated at step 365.

If, at decision step 330 the new QRS width, W(N), is not less than the baseline QRS width, W(0), then the baseline interpulse delay, D(0), is considered to be more optimal then the new interpulse delay, D(N), and the interpulse interval setting is adjusted again at step 340. At step 340, the interpulse interval is decremented by subtracting the pre-defined interval N from the baseline interpulse interval, D(0), to obtain a new, lower interpulse delay D(N), as expressed by the following equation:

$$D(N)=D(0)-N.$$

The new QRS width, W(N), associated with the new interpulse delay, D(N), is measured at step 345 and compared to the baseline QRS width, W(0), at decision step 350. Again, if the new QRS width W(N) is less than the baseline QRS width W(0), the new interpulse delay D(N) is considered more optimal than the baseline interpulse delay D(0). Thus at step 355, the interpulse delay setting is maintained at the decremented interpulse delay, D(N), and the method 300 is terminated at step 365.

If, however, at decision step 350, the new QRS width, W(N), is not less than the baseline QRS width, W(0), then the baseline interpulse delay, D(0), is still considered the optimal setting. The interpulse delay is reset to the baseline interpulse delay setting, D(0), at step 360, and the method 300 is terminated at step 365. The interpulse delay setting will remain unchanged until the next time microprocessor 60 reinitiates the method 300.

The method 300 is shown to first increment the interpulse delay and then decrement the interpulse delay in an attempt to determine if the optimal setting has changed from the baseline interpulse delay, D(0). The order in which new interpulse delays are tested is not critical to the successful operation of the present invention.

The method 300 is also shown to test only one interpulse delay longer than the baseline interpulse delay, D(0), and one interpulse delay shorter than the baseline interpulse delay, D(0). However, multiple incremental steps may be made in adjusting the interpulse delay such that two, three, or more interpulse delays greater than the baseline setting and two, three, or more interpulse delays less than the baseline setting may be tested. This testing may be accomplished by starting with an initially longer interval N by which the baseline setting, D(0), is increased or decreased. This interval N could then be progressively decreased so that new interpulse interval settings, which are progressively closer to D(0) in value, are tested. This can be referred to as a convergent, iterative algorithm.

Numerous algorithms could be used successfully within the present invention for performing a series of QRS width measurements associated with varying interpulse delay settings. Preferably, an iterative algorithm is used which allows repeated measurements to be made until the minimum QRS width measurement is found.

In alternative embodiments, other surrogate measures of cardiac performance may be implemented in the method 300 of FIG. 4. Likewise, direct measures of cardiac performance that become chronically feasible may be implemented in the method 300 of FIG. 4.

Thus a method has been described for optimizing the interpulse delay during biventricular stimulation. By selecting the interpulse delay that provides the minimum QRS width, the contraction of the left and right ventricles is expected to be better synchronized, thus improving cardiac output. By repeating this method periodically, the interpulse delay setting is adaptively adjusted over time such that if the optimal setting fluctuates with changes in disease state, medication, activity level or otherwise, the interpulse delay will always be set at the optimal setting.

The method described herein may be implemented in cardiac stimulation devices providing stimulation therapy to both the right and left ventricle without additional sensors or complex software algorithms. Though the present method is described as applicable to biventricular stimulation, it could be altered in order to optimize the interpulse delay during biatrial stimulation as well, in which optimization of the P-wave portion of the cardiac signal is achieved. In the latter situation, the device 10 performs atrial interpulse delay optimization by minimizing the P wave width as compared to the QRS width.

While the present invention has been described according to specific embodiments and applications thereof, numerous modifications and variations could be made thereto by those skilled in the art without departing from the scope of the invention.

What is claimed is:

1. An optimization method for use in a multi-chamber cardiac stimulation device, comprising:
setting a baseline interpulse delay between a stimulation of a first cardiac chamber on a right side of a heart and a stimulation of a second corresponding cardiac chamber on left side of the heart;
delivering a first stimulation to the first cardiac chamber;
delivering a second stimulation to the second cardiac chamber according to the baseline interpulse delay;

measuring a baseline width of a depolarization event associated with the baseline interpulse delay, in response to the first and second stimulations; and iteratively determining an optimal interpulse delay that results in an optimum width of the depolarization event.

2. The method of claim 1, wherein the step of iteratively determining the optimal interpulse delay includes setting the optimal interpulse delay as the baseline interpulse delay.

3. The method of claim 2, wherein the step of iteratively determining the optimal interpulse delay includes measuring the width of the depolarization event in response to an interpulse delay that is different from the baseline interpulse delay.

4. The method of claim 3, wherein the step of setting the baseline interpulse delay includes setting a stimulation delay between a left ventricle and a right ventricle of the heart.

5. The method of claim 4, wherein the step of measuring the width of the depolarization event includes measuring the width of a current QRS complex associated with a current interpulse delay.

6. The method of claim 5, wherein the step of iteratively determining the optimal interpulse delay includes comparing the width of the current QRS complex to the baseline width of the QRS complex associated with the baseline interpulse delay.

7. The method of claim 6, wherein if the width of the current QRS complex is less than the baseline width of the QRS complex, setting the current interpulse delay as the baseline interpulse delay.

8. The method of claim 5, wherein the step of measuring the width of the current QRS complex includes measuring the width of the current QRS complex during biventricular stimulation.

9. The method of claim 5, wherein the step of measuring the width of the current QRS complex includes sensing the current QRS complex using near-field sensing.

10. The method of claim 5, wherein the step of measuring the width of the current QRS complex includes sensing the current QRS complex using far-field sensing.

11. The method of claim 3, wherein the step of setting the baseline interpulse delay includes setting a stimulation delay between a left atrium and a right atrium of the heart.

12. The method of claim 11, wherein the step of measuring the width of the depolarization event includes measuring the width of a current P wave associated with a current interpulse delay.

13. The method of claim 12, wherein the step of iteratively determining the optimal interpulse delay includes comparing the width of the current P wave to the baseline width of the P wave associated with the baseline interpulse delay.

14. The method of claim 13, wherein if the width of the current P wave is less than the baseline width of the P wave, setting the current interpulse delay as the baseline interpulse delay.

15. The method of claim 12, wherein the step of measuring the width of the current P wave includes measuring the width of the current P wave during biatrial stimulation.

16. The method of claim 12, wherein the step of measuring the width of the current P wave includes sensing the current P wave using near-field sensing.

17. The method of claim 12, wherein the step of measuring the width of the current P wave includes sensing the current P wave using far-field sensing.

18. The method of claim 1, wherein the step of iteratively determining the optimal interpulse delay includes adaptively adjusting the baseline interpulse interval over time to reflect any one or more of change in a disease state, medical therapy, physical activity, or change in cardiac electromechanical response.

19. A multi-chamber cardiac stimulation device comprising:
   a plurality of electrodes;
   a sense system coupled to a plurality of electrodes, the sense system to sense a cardiac signal in a first cardiac chamber on a right of a heart and a second cardiac chamber on a left side of the heart;
   a pulse generator, connected to at least some of the plurality of electrodes, to generate stimulation energy;
   wherein at least some of the plurality of electrodes selectively deliver stimulation energy to any one or more of the first or second cardiac chambers; and
   a controller, connected to the pulse generator, that sets a predetermined baseline interpulse delay for stimulation energy delivered between the first cardiac chamber and the second cardiac chamber, that measures a baseline width of a depolarization event associated with the predetermined baseline interpulse delay, in response to the stimulation energy delivered between the first cardiac chamber and the second cardiac chamber, and that iteratively determines an optimal interpulse delay which results in an optimum width of the depolarization event.

20. The device of claim 19, further comprising a current QRS complex associated with a current interpulse delay, wherein the controller measures a width of a current QRS complex associated with a current interpulse delay and compares the width of the current QRS complex to a baseline width of the QRS complex associated with the predetermined baseline interpulse delay.

21. The device of claim 20, wherein if the width of the current QRS complex is less than the baseline width of the QRS complex, the controller sets the current interpulse delay as the predetermined baseline interpulse delay.

22. The device of claim 19, wherein the controller adaptively adjusts the predetermined baseline interpulse interval over time to reflect any one or more of change in a disease state, medical therapy, physical activity, or change in cardiac electromechanical response.

23. The device of claim 19, wherein the controller measures the width of the current QRS complex during biventricular stimulation, and wherein the pulse generator generates the stimulation energy for the biventricular stimulation.

24. The device of claim 19, wherein the controller measures the width of the current P wave complex during biatrial stimulation.

25. A bi-chamber cardiac stimulation device comprising:
   a plurality of electrodes;
   a sense system coupled to the plurality of electrodes, the sense system to sense a cardiac signal in a cardiac chamber on a right of a heart and a second corresponding cardiac chamber on a left side of the heart;
   means for generating stimulation energy;
   means for selectively delivering the stimulation energy to any one or more of the first or second cardiac chambers;
   a controller coupled to the means for generating stimulation energy, the controller to set a predetermined baseline interpulse delay between a stimulation of the first cardiac chamber and a stimulation of the second cardiac chamber;
   means for measuring a baseline width of a depolarization event associated with the predetermined baseline interpulse delay, in response to the stimulation energy delivered between the first cardiac chamber and the second cardiac chamber; and means for iteratively determining an optimal interpulse delay that results in a minimum width of the depolarization event.

26. The device of claim 25, wherein the means for measuring the baseline width of the intrinsic depolarization measures the width of a current QRS complex associated with a current interpulse delay, and compares the width of the current QRS complex to a baseline width of the QRS complex associated with the predetermined baseline interpulse delay.

27. The device of claim 25, wherein the means for iteratively determining further comprises means for setting the current interpulse delay as the predetermined baseline interpulse delay if the width of the current QRS complex is less than the baseline width of the QRS complex.

28. The device of claim 27, wherein the means for measuring the baseline width of the depolarization event measures the width of the current QRS complex during biventricular stimulation.

29. The device of claim 25, wherein the means for measuring the baseline width of the depolarization event measures the width of the current P wave during biatrial stimulation.

* * * * *